United States Patent
Winsor

(10) Patent No.: US 7,010,092 B2
(45) Date of Patent: Mar. 7, 2006

(54) DUAL ENERGY IMAGING USING OPTICALLY COUPLED DIGITAL RADIOGRAPHY SYSTEM

(75) Inventor: Robin Winsor, Calgary (CA)

(73) Assignee: Imaging Dynamics Company Ltd., Calgery (CA)

( * ) Notice: Subject to any disclaimer, the term of this patent is extended or adjusted under 35 U.S.C. 154(b) by 45 days.

(21) Appl. No.: 10/636,529

(22) Filed: Aug. 8, 2003

(65) Prior Publication Data

US 2005/0031081 A1 Feb. 10, 2005

(51) Int. Cl.
*H05G 1/64* (2006.01)
*G01T 1/20* (2006.01)

(52) U.S. Cl. ............... 378/98.9; 378/98.3; 378/98.11; 250/367; 250/368; 250/370.11

(58) Field of Classification Search ............... 378/5, 378/16, 19, 57, 98.8, 98.9, 98.11, 65, 98.3, 378/98.12; 250/367, 370.11, 368
See application file for complete search history.

(56) References Cited

U.S. PATENT DOCUMENTS

| | | | | |
|---|---|---|---|---|
| 4,247,774 A | * | 1/1981 | Brooks | 250/367 |
| 4,578,803 A | * | 3/1986 | Macovski | 378/62 |
| 4,626,688 A | * | 12/1986 | Barnes | 250/361 R |
| 4,709,382 A | * | 11/1987 | Sones | 378/62 |
| 4,792,900 A | * | 12/1988 | Sones et al. | 600/407 |
| 4,963,746 A | * | 10/1990 | Morgan et al. | 250/363.02 |
| 5,127,032 A | * | 6/1992 | Lam et al. | 378/189 |
| 5,138,167 A | * | 8/1992 | Barnes | 250/370.01 |
| 5,150,394 A | * | 9/1992 | Karellas | 378/62 |
| 5,235,191 A | * | 8/1993 | Miller | 250/486.1 |
| 5,451,793 A | * | 9/1995 | Boone | 250/486.1 |
| 5,481,584 A | * | 1/1996 | Tang et al. | 378/98.9 |

(Continued)

OTHER PUBLICATIONS

"Battle of the Detectors Defines Future of DR Market" Mar. 5, 2003, www.diagnosticimaging.com/DR/battle.shtml.

(Continued)

*Primary Examiner*—Allen C. Ho
(74) *Attorney, Agent, or Firm*—Gowling Lafleur Henderson LLP; D. Doak Horne; Brian Lee

(57) ABSTRACT

This invention relates to an optically coupled digital radiography method and apparatus for simultaneously obtaining two distinct images of the same subject, each of which represents a different x-ray energy spectrum. The two images may be combined in various ways such that anatomical features may be separated from one another to provide a clearer view of those features or of underlying structures. The two different images are obtained using a pair of scintillators separated by an x-ray filter that attenuates part of the x-ray spectrum of an x-ray exposure such that the first and second scintillators receive a different energy spectrum of the same x-ray exposure. Alternatively, the two different images can be obtained without a filter and with two scintillators made of different fluorescing materials that react differently to the same x-ray exposure.

17 Claims, 2 Drawing Sheets

U.S. PATENT DOCUMENTS

| | | | | |
|---|---|---|---|---|
| 5,550,380 | A | * | 8/1996 | Sugawara et al. ...... 250/370.11 |
| 5,570,403 | A | * | 10/1996 | Yamazaki et al. .............. 378/5 |
| 5,712,890 | A | * | 1/1998 | Spivey et al. .................. 378/37 |
| 5,723,865 | A | * | 3/1998 | Trissel et al. ................ 250/368 |
| 5,790,629 | A | * | 8/1998 | Svensson et al. ........... 378/98.7 |
| 5,864,146 | A | * | 1/1999 | Karellas ...................... 250/581 |
| 5,923,071 | A | * | 7/1999 | Saito ........................... 257/458 |
| 6,038,286 | A | * | 3/2000 | Wagli et al. ................ 378/98.3 |
| 6,064,715 | A | * | 5/2000 | Sklebitz et al. ................ 378/37 |
| 6,195,413 | B1 | * | 2/2001 | Geus et al. ................. 378/98.9 |
| 6,285,740 | B1 | * | 9/2001 | Seely et al. ................ 378/98.9 |
| 6,346,707 | B1 | * | 2/2002 | Vizard et al. ................ 250/368 |
| 6,353,657 | B1 | * | 3/2002 | Bayrock et al. ........... 378/98.3 |
| 6,392,248 | B1 | * | 5/2002 | Takahara et al. ............. 250/580 |
| 6,869,218 | B1 | * | 3/2005 | Winsor ....................... 378/207 |

OTHER PUBLICATIONS

Dual Energy Imaging Mar. 5, 2003, www.gemedicalsystem-seurope.com/euen/rad/xr/radio/products/xqi/dual_energy.html.

"Dual Energy Subtraction Radiography—Adding Critical Information to the Diagnosis of Chest Disease", Mar. 5, 2003, www.reillycomm.com/it_archive/it_toll01_2.htm.

Takeo et al., "A New FCR Image Processing Function: Energy Subtraction FCR 9501 / ES / FCR DY-A", Fuji Computed Radiography Technical Review No. 4, undated, no date.

* cited by examiner

DUAL ENERGY IMAGING USING OPTICALLY COUPLED DIGITAL RADIOGRAPHY SYSTEM

FIELD OF THE INVENTION

The present invention is directed generally to digital radiography, and in particular to an optically-coupled digital radiography system that can simultaneously acquire two images with different x-ray energy spectra for the purpose of producing separable bone and soft tissue images.

BACKGROUND OF THE INVENTION

For over a hundred years photographic films have been used to capture and display x-rays for diagnostic purposes. In recent years, digital radiography (DR) has become increasingly popular. DR refers to the application of digital equipment and image processing techniques to projection radiography. Digitally recorded x-rays are superior to those recorded with photographic film due to tile greater dynamic range offered by a digital recording system. Furthermore, computer image processing techniques provide a wealth of capabilities to study otherwise obscured details within the image.

One type of DR imaging device is an optically-coupled charge-coupled device (CCD) DR system used for clinical diagnosis. Optically coupled CCD-based DR systems use a scintillator screen, a mirror and a lens to capture and reduce an x-ray image onto a CCD camera for digitization. To take a digital radiograph using such a system, a DR imaging unit is positioned behind a subject. A standard radiographic generator positioned in front of the subject directs radiation through the subject to a fluorescent-imaging scintillator screen mounted just behind the front surface of the imaging unit. The scintillator screen is the conversion media for radiation to visible light. The scintillator screen absorbs the radiographic radiation and emits light of a particular wavelength which closely matches the peak sensitivity of a CCD camera. A front-surfaced mirror is positioned at an angle inside the imaging unit to direct the visible radiographic image into the CCD camera. The mirror allows the CCD camera to be positioned out of the direct path of the radiation, effectively shielding it from radiation exposure and prolonging its life. A high-efficiency lens is located between the mirror and camera and reduces the image and directs it onto the surface of a CCD sensor in the camera.

The visual image formed by the fluorescent-imaging screen is converted into a digital image by the CCD sensor. A control computer converts the image into a medical image file that can be viewed for clinical diagnosis, enhanced and electronically stored with patient demographic information in a picture archiving system.

Digital radiography has enabled the use of a technique known as dual energy subtraction radiography, which exploits the energy dependence of x-ray attenuation by different tissues. When producing multiple images of a subject obtained by multiple x-ray exposures at different kilovolt peak (kVp) levels and/or by a different filtering of a single x-ray exposure, the photons will interact differently in the scintillator and/or subject. The proportion of photoelectric absorption to Compton scattering will be different in the generation of the different images. Using this effect, a third image can be calculated from the two, in which for instance, the bone structure or soft tissue can be significantly enhanced or suppressed.

One known application of this technique uses a single x-ray exposure detected by two phospor-based receptor plates separated by a filter. The filter attenuates a portion of the x-ray spectrum, thereby enabling the receptor plates to produce two images of the same subject but with different kVp levels, and different contrast properties. Using these two images will make it possible, for instance, to separate the bone structures in one image from the other image, thereby generating a third image that primarily shows soft tissue. Digital imaging using phosphor-based receptor plates is laborious and time intensive as technologists typically must carry the plates to a reader and wait for the reader to energize the plates and record light flashes that correspond to the energy imparted by the x-rays that struck the plates.

A different approach to dual energy digital imaging involves digital imaging devices that use sequential x-ray exposures in rapid succession, at different kVp settings. A scintillator produces multiple images when struck by the multiple x-ray exposures, and these images are captured by a digital sensor for image processing. Because this technique involves multiple sequential exposures, the time delay between exposures tends to cause misregistration resulting in a less-than-perfect separation of the bone and soft tissue components.

Therefore, it is desirable to provide a dual energy DR technique that enjoys the accuracy obtained by using a single exposure, and the processing speed enjoyed by a scintillator-based imaging system.

SUMMARY OF THE INVENTION

According to one aspect of the invention, there is provided a DR method and apparatus for simultaneously obtaining two distinct images of the same subject, each of which represents a different x-ray energy spectrum. The two images may be combined in various ways such that anatomical features may be separated from one another to provide a clearer view of those features or of underlying structures.

In particular, there is provided an optically-coupled digital radiography system for simultaneously producing multiple images of differing energies of a subject from a single x-ray exposure of the subject. The system comprises (a) a first scintillator that produces a visible first image when subjected to an x-ray exposure of a subject;

(b) a first digital camera that is optically coupled to the first scintillator, for capturing the first image;

(c) an x-ray filter positioned in the path of the x-ray exposure and downstream of the first scintillator, for selectively attenuating a portion of the x-ray spectrum of the x-rays that have passed through the first scintillator;

(d) a second scintillator positioned in the path of the x-ray exposure and downstream of the filter and that produces a visible second image when subjected to x-rays that have passed through the filter, the second image being different than the first image; and (e) a second digital camera optically coupled to the second scintillator, for capturing the second image.

When a camera is "optically coupled" to a scintillator, an optical pathway is provided for a visible image produced by the scintillator to reach the camera. For example, the first or second camera can be located out of the path of the x-ray exposure and out of the line-of-sight of the associated scintillator. In such a case, a reflector is provided that is positioned in line-of-sight of the associated scintillator and is angled to reflect the image produced by the scintillator to the camera.

The first and second scintillators can have a fluorescing material selected from a large group of known x-ray scintillating materials such as terbium doped gadollineum oxysulfide and thallium doped cesium iodide. The first and second scintillators can each have different fluorescing materials that respond differently to the x-ray exposure, i.e. reacts to a different portion of the x-ray energy spectrum.

The x-ray filter can be a copper plate that is in adjacent parallel contact with the reflector. The copper plate can also serve as a support structure for a reflector, and in such case is coated on one major surface with a reflective layer and has sufficient thickness to attenuate the x-ray exposure and mechanically support the reflective coating.

The subject can comprise bone and tissue and the system can further comprise a computer communicative with the first and second cameras to receive the first and second images. The computer has a program that uses the first and second images to produce a bone-only or tissue-only third image, then algebraically combines the third image with the first or second images to enhance certain features in the subject. In particular, the computer comprises intensity reference tables that associates one or more bone-tissue ratios with a pixel intensity in a plurality of pixel intensities, and the program is programmed to use the intensity reference tables to determine the actual bone-tissue ratio in the subject, then to produce a bone-only or tissue only third image from the actual bone-tissue ratio.

According to another aspect of the invention, there is provided an optically-coupled digital radiography system comprising:

(a) a first scintillator comprising a first fluorescing material that produces a visible first image when subjected to an x-ray exposure, (b) a first digital camera optically coupled to the first scintillator, for capturing the first image;

(c) a second scintillator positioned in the path of the x-ray exposure and downstream of the first scintillator and comprising a second fluorescing material that responds sufficiently differently to the x-ray exposure than the first scintillator material to produce a visible second image that is different from the first image; and (d) a second digital camera optically coupled to the second scintillator for capturing the second image.

In this aspect of the invention, there is no filter that attenuates the x-ray beam before reaching the second scintillator. The differences in the first and second images result from use of two different fluorescing scintillator materials, wherein each material intercepts and reacts to a different portion of the energy spectrum. Suitable scintillator materials include $CaWO_4$, $BaPbSO_4$, $BaFCl:Eu$, $LaOBr:Tm$, $Y_2O_2S:Tb$, $CsI:Tl$, $Gd_2O_2S:Tb$, $BaSrSO_4:Eu$. In order to choose a suitable pair of materials for the scintillators, consideration is given to the portion of the x-ray spectrum to which the materials are most sensitive. By choosing pairs of materials which are as distinct as possible in their x-ray characteristics, the greatest difference will be obtained between the two images. This in turn allows for the least ambiguous separation of the density components by reference to reference tables which chart the possible combinations of bone and soft tissue which can give rise to the observed pixel intensities within the image. One such feasible combination is $CsI:Tl$ and $Gd_2O_2S:Tb$.

DETAILED DESCRIPTION

Figure 1:
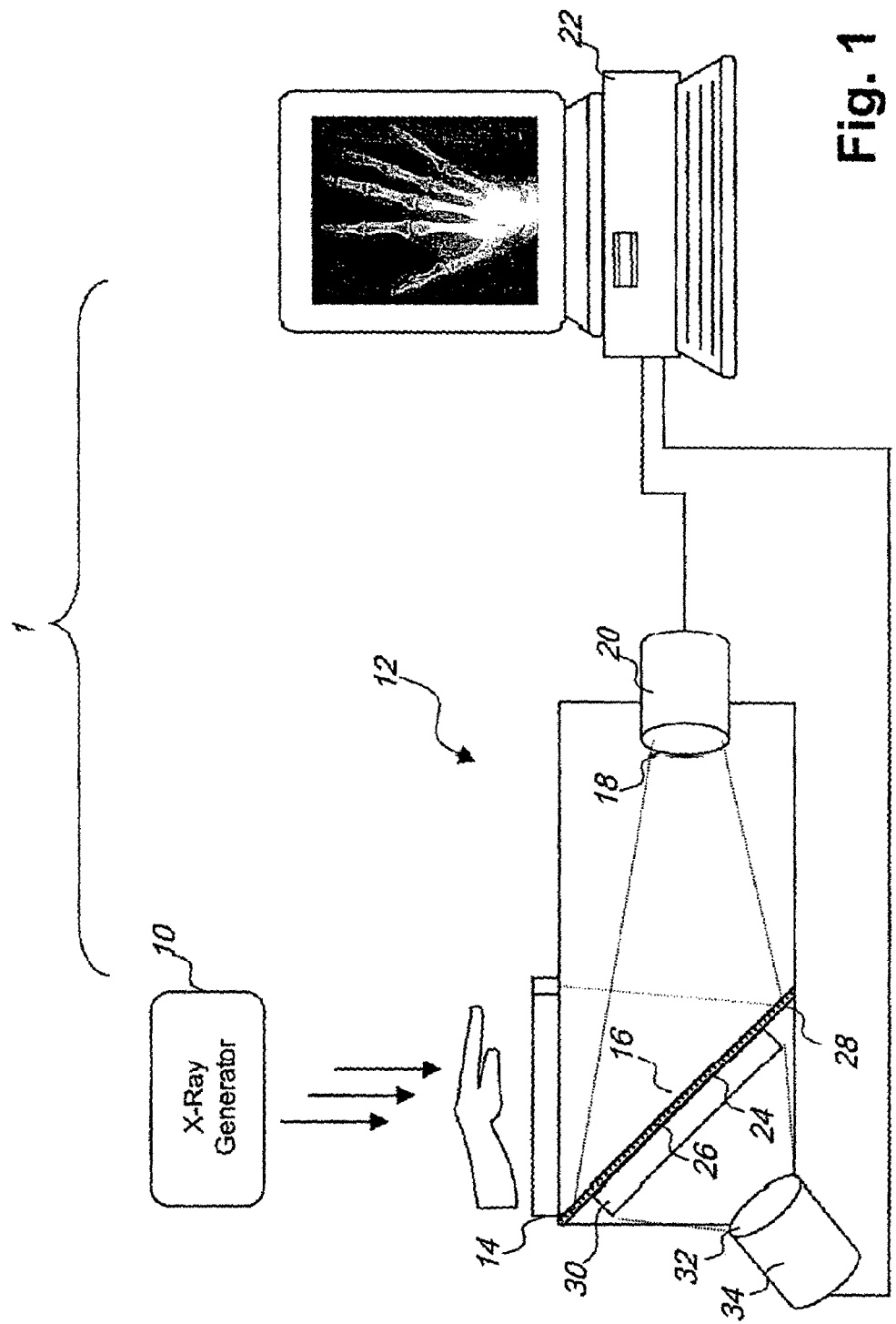
FIG. 1 is a schematic illustration of one embodiment of a dual energy DR system having an x-ray filter interposed between two scintillators constructed of the same scintillator material.

Referring to FIG. 1 and according to one embodiment of the invention, an optically-coupled CCD-based DR system 1 is provided for taking digital x-ray images of a subject, such as a human patient, for clinical diagnostic purposes.

The system 1 is operable to simultaneously obtain two distinct images of a subject, each of which represents a different x-ray energy spectrum. The two images can be algebraically combined in various ways during image processing, such that anatomical features can be separated from one another to provide a clearer view of certain features of underlying structures. In particular, one image can be algebraically combined with another to produce a third image that enhances the bone structure or muscle tissue in the subject.

In particular, the two different-energy images obtained by the system 1 can be processed to produce a third image showing only bone or only soft tissue. The process uses a set of intensity reference tables provided for each scintillator response to the varying bone/tissue ratios, to identify the actual ratio of bone-to-tissue of the subject in the two images. Once so identified, the system 1 can delete the bone to produce a tissue-only third image, or delete the tissue to produce a bone-only third image. This third image can then be algebraically combined with the first or second image to enhance certain details in those images, for example, a bone-only third image can be subtracted from the first image to suppress the bone detail and enhance the soft tissue detail in the first image.

The system 1 has an x-ray source 10 that sends x-rays through a subject. When a patient is in position and a part of the patient's body selected for imaging has been set in place, the x-ray source 10 is turned on and x-rays are directed towards the patient. X-rays in a single exposure from the x-ray source 10 pass through the patient and are captured by a detector 12 and converted into two digital x-ray images. In particular, some of the x-rays reaching the detector 12 are first converted into visible light by a first scintillator 14 positioned orthogonal to the x-ray source 10. The visible light forms a visible image which is reflected by a mirror 16 towards lenses in a first lens assembly 18, which reduces and directs the image onto the surface of a first CCD camera 20, which then converts the image into a first digital image. The first digital image is then transmitted to a computer 22 for image processing and storage.

In this embodiment, the mirror is positioned at a 45 degree angle to the first scintillator 14, and the first camera 20 is positioned in line of sight of the reflected image and out of the path of the x-ray exposure. Alternatively, the first camera 20 can be positioned at other locations inside the detector 12 so long as it is out of path of the x-ray exposure or if in the path of the x-ray exposure, is properly shielded When the camera is positioned in such an alternative position, the mirror angle and lens assembly focal point are adjusted accordingly.

The first scintillator 14 is made of a material which fluoresces when struck by x-rays, such as terbium doped gadollineum oxysulfide or thallium doped cesium iodide. There are many other suitable scintillator materials, such as $CaWO_4$, $BaPbSO_4$, $BaFCl{:}Eu$, $LaOBr{:}Tm$, $Y_2O_2S{:}Tb$, $BaSrSO_4{:}Eu$ and others as known in the art. All emit light during this reaction when they are struck by x-rays.

The mirror 16 comprises an x-ray transparent support layer 24 coated on one major surface with a thin reflective layer 26 and on its other surface with a filter layer 28. In this embodiment, the support layer 24 composition is plastic, the reflective layer 26 composition is aluminum, and the filter layer 28 composition is copper. In particular, the copper filter layer 28 has a thickness of about 0.5 mm; however, any suitable metal filter layer as known in the art may be substituted. Alternatively, the mirror 16 comprises a metal layer that serves as both a support layer and filter layer, and a reflective layer coating one side of the metal layer.

X-rays that are not attenuated by the first scintillator 14 reach the mirror 16. Most of these x-rays pass through the support and reflective layers 24, 26, as these materials have low attenuation characteristics, and reach the copper filter layer 28. The filter layer 28 absorbs most of the lower energy x-rays, such that the x-rays that pass through the filter layer are predominantly high-energy x-rays. In other words, the filter layer 28 serves to "harden" the x-ray beam.

The predominantly high energy x-rays in the hardened beam then continue through the filter layer 28 and reach a second scintillator 30 mounted to the filter side of the mirror 16. In this embodiment, the second scintillator 30 is made of the same material as the first scintillator 14. The x-rays activate the second scintillator 30, causing it to emit a second visible image. As compared to the first scintillator 14, the second scintillator is exposed to more of the predominantly high energy x-rays, and therefore, the visible image produced by the second scintillator 30 ("high energy image") has different contrast properties compared to the visible image produced by the first scintillator 14 ("low energy image").

This high energy image is then reduced by a second lens assembly 32: the reduced image is then directed onto the surface of a second CCD camera 34, which converts the visual image into a second digital image. The second digital image is then transmitted to the computer 22 for imaging processing and storage. The second CCD camera 34 is mounted facing the second scintillator 30 and out of the path of the x-ray source 10. Alternatively, the second camera 34 can be positioned at other locations inside the detector 12 so long as it is out of path of the x-ray exposure, or if in the path of the x-ray exposure, is properly shielded. When the camera is positioned in such an alternative position, a second mirror can be provided and the second lens assembly focal point can be adjusted accordingly.

In this embodiment, the filter layer 28 is in adjacent parallel contact with the support layer 24 and the second scintillator 30 is in adjacent parallel contact with the filter layer 28; however, the filter layer 28 and second scintillator 30 can be positioned differently, so long as they are in the path of the x-ray exposure, e.g. the filter layer 28 and second scintillator 30 can be placed parallel to the first scintillator 14 and orthogonal to the x-ray source 10 (not shown). In this alternative configuration, a second mirror (not shown) is provided to reflect the visible image produced by the second scintillator 30 to the second CCD camera 34.

The x-ray source 10, scintillators 14, 30, lens assemblies 18, 32 and CCD cameras 20, 34 are per se known in the art, and for example, can be those manufactured by Imaging Dynamics Company Ltd for their Xplorer 1700 detector.

Once the high and low energy images have been acquired, the computer 22 can then run a program that eliminates the bone or soft tissue components from an image altogether, by using a set of intensity reference tables provided for each scintillator response to the varying bone/tissue ratios to identify the actual ratio of bone-to-tissue of the subject in the two images. The reference tables comprise a set of bone/tissue ratios associated with a set of pixel intensities, and are stored in memory on a computer 22 for use during image processing. The reference tables are constructed from exposures of multiple test subjects. The different test subjects represent different ratios of bone to tissue, and comprise different ratios of a first material such as aluminum to represent bone density, and a second material such as Lucite to represent soft tissue density. The exposures of these test subjects activate a scintillator, which in turn emits visible light for capture by a CCD camera. The intensity of each pixel in each exposure is recorded and associated with the exposed test subject, and thus to the bone-to-tissue ratio associated with that test subject.

To determine the actual bone/tissue ratio of the imaged subject, the computer 22, for each image A, correlates the measured intensity $I_A$ of each pixel $P_{A[i,j]}$ at positions [i,j] in the image A to one or more bone-tissue ratios in the reference map. As there can be multiple bone-tissue ratios for each pixel intensity, the computer 22 compares the associated bone-tissue ratios for the pixel $P_{1[i,j]}$ in the first image to the bone-tissue ratios for the pixel $P_{2[i,j]}$ in the second image. As images 1 and 2 represent the same subject, the bone/tissue ratio common to both images 1,2, will be selected as the actual bone-tissue ratio of the imaged subject. Knowing this ratio, a new image showing only bone or only soft tissue can be constructed. This new image can then be algebraically combined with the first or second image to enhance certain details in those images; for example, a bone-only image can be subtracted from the first image to suppress the bone detail and enhance the soft tissue detail in the first image.

For example, if a pixel $P_1$ at position i,j in the first image has intensity $I_1$, it may be seen from look up table $R_1$ of reference values for a first scintillator to represent either $x_1$ millimeters of bone and $y_1$ millimeters of soft tissue or $x_2$ millimeters of bone and $y_2$ millimeters of soft tissue. Pixel $P_2$ at position i,j in the second image has a different intensity $I_2$ which from the reference table $R_2$ for a second scintillator may represent either $x_2$ millimeters of bone and $y_2$ millimeters of soft tissue or $x_3$ millimeters of bone and $y_3$ millimeters of soft tissue. Given that both pixels $P_1$ and P2 represent the same anatomy, they must represent the same ratio of bone to soft tissue. The correct ratio is therefore the one candidate common to both tables, $x_2$ and $y_2$. Other methods can also be used but all are dependent on having two images of the same subject imaged with different responses to the incident beam. It should be noted that the different response may be due to either a difference in the beam or a difference in the receptor.

Figure 2:
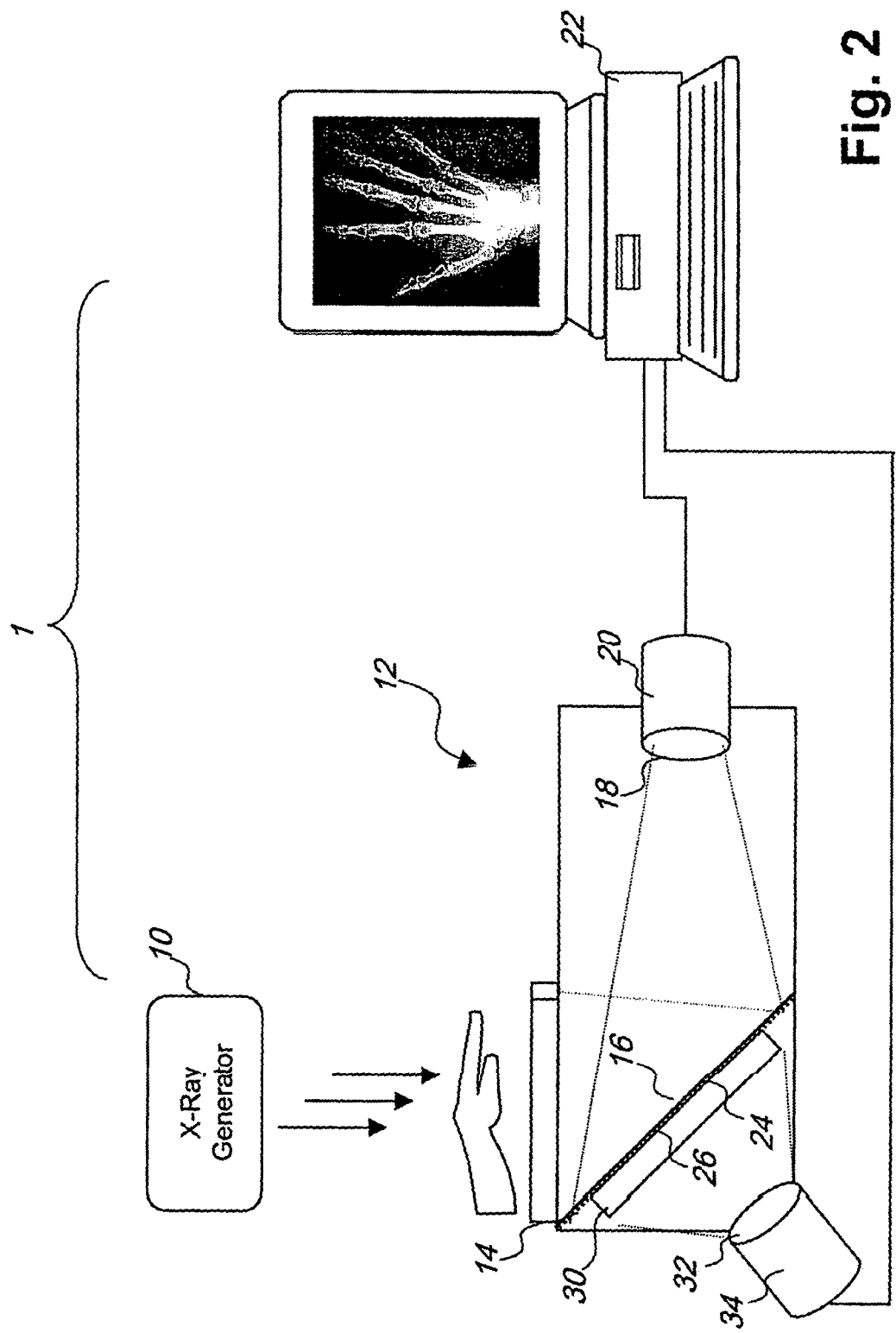
FIG. 2 is a schematic illustration of a second embodiment of a dual energy DR system having a pair of scintillators constructed of different scintillator materials.

According to a second embodiment of the invention and referring to FIG. 2, the system 1 omits the filter layer 28 used in the first embodiment and instead uses different scintillator materials for the two scintillators 14, 30 to produce different visible images. In particular, the first scintillator 14 is composed of thallium doped cesium iodide while the second scintillator 30 is composed of terbium doped gadolineum oxysulfide. The two materials respond differently to the incident x-ray beam and thereby provide the two distinct data sets required for the dual energy separation. The reference tables in the computer are modified to include a set of intensity reference tables for the second scintillator's 30 response to the varying bone/tissue ratios. There are many suitable scintillator materials, such as $CaWO_4$, $BaPbSO_4$, BaFCl:Eu, LaOBr:Tm, $Y_2O_2S$:Tb, CsI:Tl, $Gd_2O_2S$:Tb, $BaSrSO_4$:Eu and others as known in the art in which pairs of materials may be chosen for the two scintillators 14, 30. In order to choose a suitable pair of materials for the scintillators 14, 30, consideration is given to the portion of the x-ray spectrum to which the materials are most sensitive. By choosing pairs of materials which are as distinct as possible in their x-ray characteristics, the greatest difference will be obtained between the two images. This in turn allows for the least ambiguous separation of the density components by reference to look up tables which chart the possible combinations of bone and soft tissue which can give rise to the observed pixel intensities within the image. The principal factor in determining the difference in absorption of the materials is the atomic number. The photoelectric absorption edge of the material becomes more pronounced as the atomic number of the absorber increases.

According to a third embodiment of the invention, the system 1 comprises both the beam hardening filter layer 28 of the first embodiment and the different scintillators 14, 30 of the second embodiment to produce two different visible images.

While the preferred embodiment of the invention has been illustrated and described, it will be appreciated that various changes can be made therein without departing from the scope and spirit of the invention.

What is claimed is:

1. An optically-coupled digital radiography system for simultaneously producing multiple images of differing energies of a subject from a single x-ray exposure of the subject, the system comprising:
   (a) a first scintillator that produces a visible first image when subjected to an x-ray exposure of a subject;
   (b) a first digital camera optically coupled to the first scintillator for capturing the first image;
   (c) an x-ray filter positioned in the path of the x-ray exposure and downstream of the first scintillator, for selectively attenuating a portion of the x-ray spectrum of the x-rays that have passed through the first scintillator, wherein the x-ray filter is coated with a reflective coating and is angled to reflect the first image from the first scintillator to the first camera;
   (d) a second scintillator positioned in the path of the x-ray exposure and downstream of the filter and that produces a visible second image when subjected to x-rays that have passed through the filter, the second image being different than the first image; and
   (e) a second digital camera optically coupled to the second scintillator for capturing the second image.

2. The system of claim 1 wherein the first and second scintillators have a fluorescing material selected from the group of $CaWO_4$, $BaPbSO_4$, BaFCl:Eu, LaOBr:Tm, $Y_2O_2S$:Tb, CsI:Tl, $Gd_2O_2S$:Tb, and $BaSrSO_4$:Eu.

3. The system of claim 2 wherein the first and second scintillators each have different fluorescing materials that respond differently to the x-ray exposure.

4. The system of claim 1 wherein the x-ray filter is a copper plate.

5. The system of claim 1 wherein the second digital camera is positioned out of the path of the x-ray exposure.

6. The system of claim 1 wherein the x-ray filter is a copper plate and has sufficient thickness to attenuate the x-ray exposure to produce a different second image, and to mechanically support the reflective coating.

7. An optically-coupled digital radiography system for simultaneously producing multiple images of differing energies of a subject from a single x-ray exposure of the subject, the system comprising:
   (a) a first scintillator that produces a visible first image when subjected to an x-ray exposure of a subject;
   (b) a first digital camera positioned out of the path of the x-ray exposure and optically coupled to the first scintillator for capturing the first image;
   (c) an x-ray filter positioned in the path of the x-ray exposure and downstream of the first scintillator, for selectively attenuating a portion of the x-ray spectrum of the x-rays that have passed through the first scintillator;
   (d) a second scintillator positioned in the path of the x-ray exposure and downstream of the filter and that produces a visible second image when subjected to x-rays that have passed through the filter, the second image being different than the first image;
   (e) a second digital camera positioned out of the path of the x-ray exposure and optically coupled to the second scintillator for capturing the second image; and
   (f) said first digital camera positioned so as to capture said first image without said first image ever having been combined with said second image.

8. The system as claimed in claim 7 further comprising a first reflector optically coupled to the first scintillator and the first digital camera, and a second reflector optically coupled to the second scintillator and the second digital camera.

9. The system as claimed in claim 8 wherein the first and second scintillators are substantially parallel and the first and second reflectors are positioned to reflect light from the first scintillator to the first camera and from the second scintillator to the second camera.

10. An optically-coupled digital radiography system for simultaneously producing multiple images of differing energies of a subject from a single x-ray exposure of the subject, the system comprising:
    (a) a first scintillator comprising a first fluorescing material that produces a visible first image when subjected to an x-ray exposure of a subject,
    (b) a first digital camera positioned out of the path of the x-ray exposure and optically coupled to the first scintillator, for capturing the first image;
    (c) a second scintillator positioned in the path of the x-ray exposure and downstream of the first scintillator and comprising a second fluorescing material that responds sufficiently differently to the x-ray exposure than the first fluorescing material, to produce a visible second image that is different from the first image;
    (d) a second digital camera positioned out of the path of the x-ray exposure and optically coupled to the second scintillator, for capturing the second image; and
    (e) said first digital camera positioned so as to capture said first image without said first image ever having been combined with said second image.

11. The system of claim 10 further comprising an x-ray filter positioned in the path of the x-ray exposure and between the first and second scintillators, for selectively attenuating a portion of the x-ray spectrum of the x-rays that have passed through the first scintillator.

12. The system of claim 11 wherein the x-ray filter is comprised of copper.

13. The system of claim 11 wherein the x-ray filter is coated with a reflective coating and is angled to reflect the first image from the scintillator to the first camera.

14. The system of claim 13 wherein the x-ray filter is a copper plate and has sufficient thickness to attenuate the x-ray exposure to produce a different second image, and to mechanically support the reflective coating.

15. The system of claim 10 wherein the fluorescing materials for the first and second scintillators are selected from the group $CaWO_4$, $BaPbSO_4$, $BaFCl:Eu$, $LaOBr:Tm$, $Y_2O_2S:Tb$, $CsI:Tl$, $Gd_2O_2S:Tb$, and $BaSrSO_4:Eu$.

16. An optically-coupled digital radiography system for simultaneously producing multiple images of differing energies of a subject from a single x-ray exposure of the subject, the system comprising:
   (a) a first scintillator comprising a first fluorescing material that produces a visible first image when subjected to an x-ray exposure of a subject,
   (b) a first digital camera positioned out of the path of the x-ray exposure and optically coupled to the first scintillator, for capturing the first image;
   (c) a second scintillator positioned in the path of the x-ray exposure and downstream of the first scintillator and comprising a second fluorescing material that responds sufficiently differently to the x-ray exposure than the first fluorescing material, to produce a visible second image that is different from the first image;
   (d) a second digital camera positioned out of the path of the x-ray exposure and optically coupled to the second scintillator, for capturing the second image; and
   (e) a first reflector optically coupled to the first scintillator and the first digital camera, and a second reflector optically coupled to the second scintillator and the second digital camera.

17. The system as claimed in claim 16 wherein the first and second scintillators are substantially parallel and the first and second reflectors are positioned to reflect light from the first scintillator to the first camera and from the second scintillator to the second camera.

* * * * *